United States Patent [19]

May

[11] Patent Number: 5,080,676
[45] Date of Patent: Jan. 14, 1992

[54] ATTACHMENT DEVICE

[75] Inventor: Denis R. W. May, Middlesex, United Kingdom

[73] Assignee: University College London, London, United Kingdom

[21] Appl. No.: 422,425

[22] Filed: Oct. 17, 1989

[30] Foreign Application Priority Data

Oct. 18, 1988 [GB] United Kingdom ............ 8824384.5

[51] Int. Cl.$^5$ .................. A61F 2/38; A61F 2/30; A61F 2/32
[52] U.S. Cl. ........................ 623/20; 623/18; 623/22; 623/23
[58] Field of Search ............ 623/16, 18, 20, 21, 623/22, 23

[56] References Cited

U.S. PATENT DOCUMENTS

| 3,874,003 | 4/1975  | Moser et al. |        |
|-----------|---------|--------------|--------|
| 3,903,549 | 9/1975  | Deyerle      |        |
| 4,100,626 | 7/1978  | White        | 623/21 |
| 4,207,627 | 6/1980  | Cloutier     |        |
| 4,666,450 | 5/1987  | Kenna        | 623/22 |
| 4,705,520 | 11/1987 | Ahrens       | 623/18 X |

FOREIGN PATENT DOCUMENTS

| 0000549 | 2/1979  | European Pat. Off. | 623/18 |
| 0011665 | 6/1980  | European Pat. Off. | 623/20 |
| 0017743 | 12/1980 | European Pat. Off. | |
| 0024442 | 3/1981  | European Pat. Off. | |
| 0032828 | 7/1981  | European Pat. Off. | |
| 0246050 | 11/1987 | European Pat. Off. | |
| 2839093 | 3/1980  | Fed. Rep. of Germany | 623/20 |
| 8605597 | 5/1986  | Fed. Rep. of Germany | |
| 2384489 | 10/1978 | France | |
| 2391711 | 12/1978 | France | |
| 2601873 | 1/1988  | France | 623/20 |
| 2616060 | 12/1988 | France | |
| 1521679 | 8/1978  | United Kingdom | |
| 1585672 | 3/1981  | United Kingdom | |

Primary Examiner—Ronald Frinks
Attorney, Agent, or Firm—Oblon, Spivak, McClelland, Maier & Neustadt

[57] ABSTRACT

A human joint implant, for example a knee prosthesis has a working part formed with a stub having a conical profile that snap-fits into a stem that forms an anchorage in a bone cavity. The stub may carry a stud at its end that is a snap-fit into a ferrule. A flanged sleeve fits between the stub and a conical socket part of the stem.

6 Claims, 1 Drawing Sheet

ATTACHMENT DEVICE

BACKGROUND OF THE INVENTION

1. Field of the Invention

The invention relates to an attachment device particularly, though not exclusively for attachment of an elbow hip or knee prosthesis to an adjacent bone.

When a joint prosthesis is implanted in a human patient after a period of time failure may occur either in the working parts of the joint or in the anchorage between the joint and the adjacent bone. A requirement may arise to leave the anchor in place and replace the working parts of the joint, or to leave the joint in place and replace the anchor. Up to the present time, however, the anchoring parts and the working parts of the joint have not been provided as separate components because there has not been proposed a simple but strong mechanism for connecting an anchor to a working part of the joint.

SUMMARY OF THE INVENTION

This invention provides a human joint implant having a working part that is a snap-fit into a bone anchor part.

The invention also provides an implant for fitting into a bone of a patient comprising a first member having a longitudinal axis for fitting into the bone along said longitudinal axis, a second member for attachment to the first member, portions of the first and second members defining a cone and socket joint for connection together generally along said longitudinal axis, and means for releasably latching the first and second members together on insertion of the cone into the socket.

The first and second members are normally of a cobalt/nickel/molybedum alloy such as Stellite or other physiologically acceptable metallic material in which case these members are preferably separated by a flanged sleeve of non-metallic material that fits between the cone and socket portion of the joint. Thus, the flanged sleeve may be of ultra high molecular weight polyethylene or other physiologically acceptable material.

In a preferred attachment structure, the releasable latching means acts between an end of the cone and the base of the socket to hold the first and second members against movement axially apart while permitting relative rotation of the members generally about their longitudinal axes. Thus the end of the cone may have a divergent male connecting stud extending axially therefrom that snap-fits into a non-metallic female connector at the base of the socket.

BRIEF DESCRIPTION OF THE DRAWINGS

An embodiment of the invention will now be described, by way of example only with reference to the accompanying drawings in which.

DESCRIPTION OF THE PREFERRED EMBODIMENT

Figure 1:
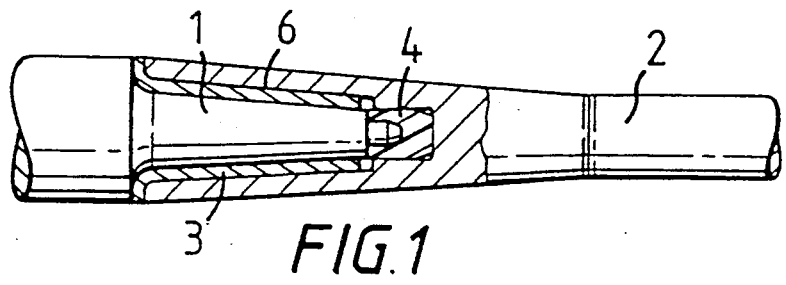
FIG. 1 is a section of a snap-fit mechanism for attaching one half of a human joint prosthesis to adjacent bone.
Figure 2:
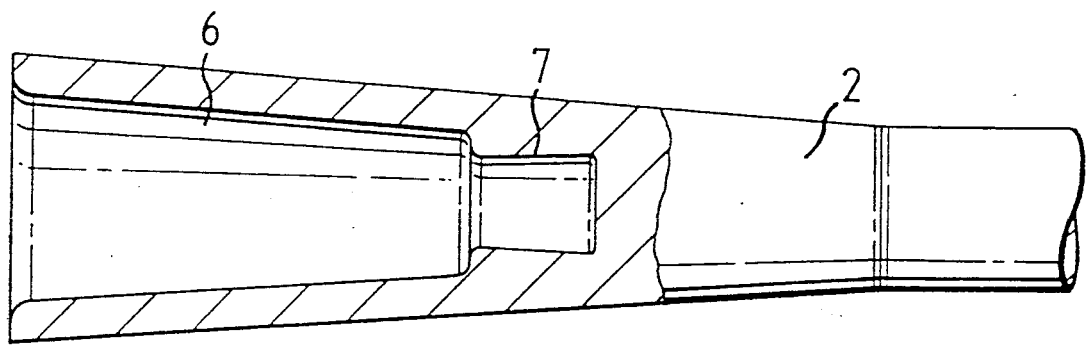
FIG. 2 is a partly sectioned view of a stem forming part of the joint of FIG. 1.
Figure 3:
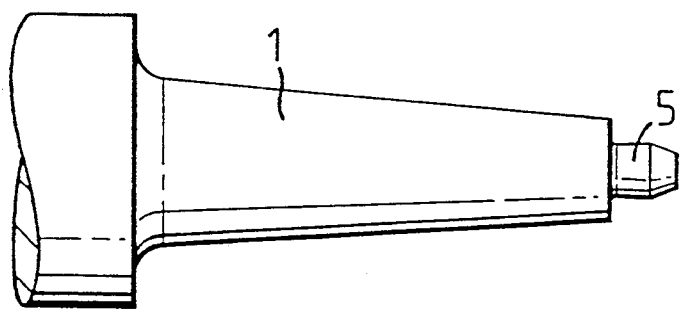
FIG. 3 is a side view of a stub forming part of the joint.
Figure 4:
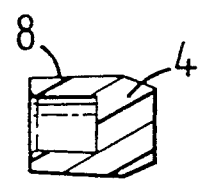
FIG. 4 is a section of a ferrule.

In the drawings, a hinge part of an artifical knee or hip joint has a stub 1 of conical profile projecting from its blind face. The stub 1 terminates at a relatively small outwardly diverging stud 5.

The stub 1 fits into a stem 2 that forms an anchorage into a cavity in the bone in which the stem 2 is either a push-fit or is cemented. The stem 2 terminates at a socket 6 of conical form having a small outwardly tapered recess 7 at its blind end. A locking ferrule 4 of plastics material has a tapered side surface 8 that matches the taper of the recess 7 so that the ferrule 4 is a snap-fit in the recess 7. A flanged tapered sleeve 3 of conical profile fits between the stub 1 and the socket 6. When the stub 1 is inserted into the socket 6, the stud 5 at its end is a snap-fit into the ferrule 4. If either the working part of the joint or the stem 2 have to be removed during the life of the prosthesis the stub 1 can be pulled from the stem 2.

Although the stub 1 and stem 2 are held only lightly together against movement axially apart, this is not a problem in practice particularly in leg joints, because bones are subject to compressive and tortional loads but not significantly to tensile loads.

I claim:

1. An implant for fitting to a bone of a patient comprising a first member having a longitudinal axis for fitting into the bone along said longitudinal axis, a second member for attachment to the first member, portions of the first and second members defining a cone and socket joint for connection together generally along said longitudinal axis, and means for releasably latching the first and second members together upon insertion of the cone into the socket, said latching means comprising inter-engaging means at the end of the cone and the base of the socket that snap fit together to hold the first and second members against movement axially apart while permitting relative rotation of the first and second member generally about said longitudinal axis, wherein the end of the cone has a divergent male connector that snap fits into a non-metallic female connector at the base of the socket.

2. A implant according to claim 1, wherein a flanged sleeve of non-metallic material fits between the cone and socket portions of the joint.

3. An implant according to claim 2, wherein the flanged sleeve is of a physiologically acceptable plastics material.

4. An implant according to claim 1, which is part of a prosthetic joint.

5. An implant according to claim 4, which is part of a knee joint.

6. An implant according to claim 4, which is part of a hip joint.

* * * * *